United States Patent
Rock et al.

[11] Patent Number: 6,032,120
[45] Date of Patent: Feb. 29, 2000

[54] ACCESSING STORED ULTRASOUND IMAGES AND OTHER DIGITAL MEDICAL IMAGES

[75] Inventors: David A. Rock, Ann Arbor, Mich.; Jeffrey S. Hastings, Los Altos, Calif.

[73] Assignee: Acuson Corporation, Mountain View, Calif.

[21] Appl. No.: 08/991,748

[22] Filed: Dec. 16, 1997

[51] Int. Cl.[7] .................................................. G06F 17/60
[52] U.S. Cl. .................................................................. 705/2
[58] Field of Search ................................. 705/2; 235/375, 235/470; 250/582; 358/403; 600/437

[56] References Cited

U.S. PATENT DOCUMENTS

| | | | |
|---|---|---|---|
| 4,857,716 | 8/1989 | Gombrich et al. | 235/375 |
| 4,958,283 | 9/1990 | Tawara et al. | 382/131 |
| 5,140,518 | 8/1992 | Ema | 600/300 |
| 5,264,684 | 11/1993 | Weil | 235/375 |
| 5,272,625 | 12/1993 | Nishihara et al. | 707/1 |
| 5,303,148 | 4/1994 | Mattson et al. | 600/437 |
| 5,321,520 | 6/1994 | Inga et al. | 358/403 |
| 5,334,851 | 8/1994 | Good et al. | 250/582 |
| 5,418,355 | 5/1995 | Weil | 235/375 |
| 5,597,995 | 1/1997 | Williams et al. | 235/375 |

*Primary Examiner*—Emanuel Todd Voeltz
*Assistant Examiner*—Thomas A. Dixon
*Attorney, Agent, or Firm*—Brinks Hofer Gilson & Lione

[57] ABSTRACT

A system and method are provided for accessing stored ultrasound images and other digital medical images. A client application sends a request comprising information identifying a unique medical study to a server application. The information identifying a particular study can be in the form of a patient accession number and can be provided to the client application with a keyboard or an automatic information reader, such as a bar-code reader, a camera, or a voice recognition device. Upon receiving the request, the server application automatically sends the client application a digital medical image associated with the study. The client application then displays the digital medical image to the user.

25 Claims, 4 Drawing Sheets

ACCESSING STORED ULTRASOUND IMAGES AND OTHER DIGITAL MEDICAL IMAGES

BACKGROUND

Medical image management systems allow medical personnel to locate, access, and display stored digital medical images. These systems typically comprise at least two networked computer components: a client device (e.g., a medical imaging review station) and a server device (e.g., a study repository server). One conventional method of accessing and displaying images requires the user to take at least two actions. First, using a keyboard, the user must manually enter information into a client device that will identify a particular patient and/or medical study. A client application in the client device then sends a search command containing the entered information to a server application on the server device. The server application locates all the studies that satisfy the search criteria and sends a list of these studies back to the client application for display to the user. The user then must select a desired study from the list, even if only one study is displayed, such as when only one study is associated with a particular patient or when the user enters enough information to identify a single study. After the user makes his selection, the client application sends a request to the server application to retrieve the digital medical images associated with the selected study. Upon receiving the request, the server application sends the images to the client application for display to the user.

There are several disadvantages to this conventional method. First, because the conventional method requires at least two user actions, the access-and-display process can take several minutes to perform. Second, because the user must push buttons, enter search criteria, and review results, the conventional method requires the user to have system-specific knowledge about the image management system. Third, because the conventional method requires the user to manually type identification information via a keyboard and visually review the results of a search, the process of locating, retrieving, and displaying digital medical images is susceptible to typographical and other operator errors.

There is, therefore, a need for a system and method for accessing stored digital medical images that will overcome the problems described above.

SUMMARY

The present invention is directed to a system and method for accessing stored digital medical images. According to a first aspect of the invention, a system and method are provided for accessing and displaying a stored digital medical image by sending a request comprising information identifying a medical study from a client application to a server application, using the server application to automatically send the client application a digital medical image associated with the study, and then using the client application to display the digital medical image. In one embodiment, the information used in the request is not provided by the server application. In another embodiment, the request is the only request sent from the client application during the accessing-and-displaying process to identify the desired medical study.

According to a second aspect of the invention, a system and method are provided for accessing and displaying a stored digital medical image using a bar-code reader to automatically input information identifying a medical study into a client application, sending a request comprising the information from the client application to a server application, using the server application to automatically send the client application a digital medical image associated with the medical study, and then using the client application to display the digital medical image.

According to a third aspect of the invention, an apparatus and method are provided for forming a request for a medical study. A bar-code reader is used to receive a bar-code image comprising information identifying a medical study, and a client application is used to form a request for a medical study using the information.

The preferred embodiments of the invention will now be described with reference to the attached drawings.

DETAILED DESCRIPTION OF THE PRESENTLY PREFERRED EMBODIMENTS

Figure 1:
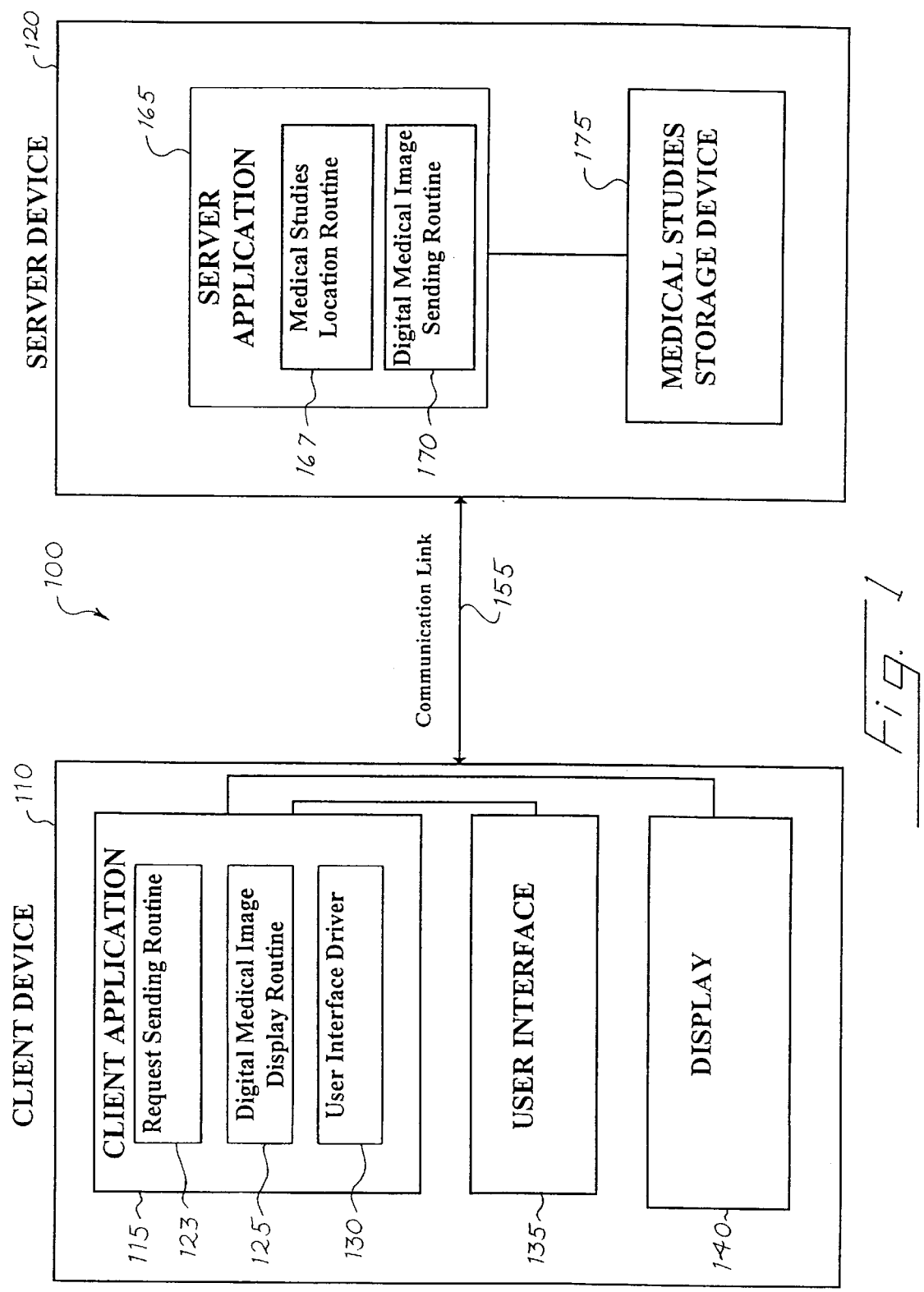
FIG. 1 is a block diagram of a client-server system of a preferred embodiment.

Turning now to the drawings, FIG. 1 is a block diagram of a client-server system 100 of a preferred embodiment. As shown in FIG. 1, a client device 110 is coupled with a server device 120 with a communication link 155. The communication link 155 can directly couple the client 110 and server 120 devices or can indirectly couple the devices 110, 120 through a data network comprising any number of intermediate computer data network devices, such as a network hub. The communication link 155 supports the transfer of medical studies between the client 110 and server 120 devices. As used herein, "medical studies" include non-image information (e.g., a patient's name and/or hospital identification, a physician's diagnosis, etc.) and digital medical images (i.e., digital images that are generated by medical imaging equipment).

The client device 110 of FIG. 1 comprises a client application 115 coupled with a user interface 135 and a display 140. The client application 115 comprises a request sending routine 123 for sending a request for a particular medical study to a server application 165 in the server device 120, a digital medical image display routine 125 for displaying an image on the display 140, and a user interface driver 130 for accepting commands from the user interface 135. The server device 120 of FIG. 1 comprises a server application 165 and a medical studies storage device 175, which can store image and non-image data. The server application 165 comprises a medical study location routine 167, which locates the requested medical study, and a digital medical image sending routine 170, which automatically sends the client application 115 a digital medical image associated with the requested study. It is preferred that these routines be implemented with software and that the client 110 and server 120 devices comprise the necessary hardware components (such as a CPU) to run the software. It is also preferred that an AEGIS™ Medical Imaging Review Station and an AEGIS™ Study Repository Server from Acuson Corporation be used as the client 110 and server 120 devices, respectively.

Figure 2:
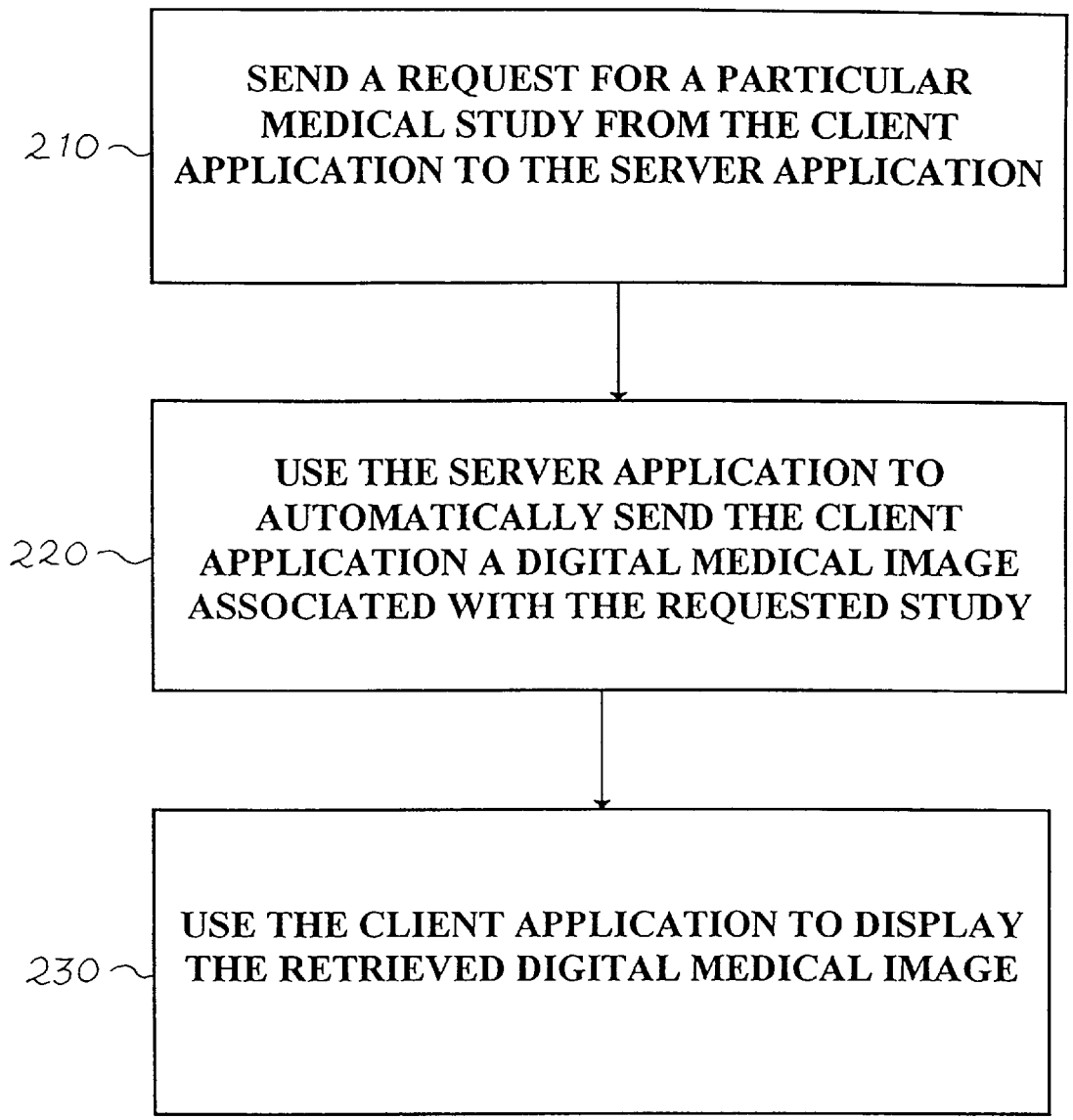
FIG. 2 is a flow chart of a method of a preferred embodiment for accessing and displaying a digital medical image.

The client-server system 100 of FIG. 1 can be used in a method for accessing and displaying a digital medical image. As shown in the flow chart of FIG. 2, this method comprises the steps of sending a request for a particular medical study from the client application 115 to the server application 165 (step 210), using the server application 165 to automatically send the client application 115 a digital medical image associated with the requested study (step 220), and using the client application 115 to display the retrieved digital medical image (step 230). The steps of this method will be described in more detail below.

First, a user enters information identifying a particular medical study using the user interface 135, which provides the information to the client application 115 via the user interface driver 130. This information can be in the form of, for example, a study accession number (i.e., a string of alpha-numeric characters that is typically generated by a hospital's medical information system to uniquely identify a particular medical study). With the provided information, the client application 115 (using the request sending routine 123) sends a request for the desired medical study to the server application 165 (step 210). The medical study location routine 167 searches the non-image data stored in the storage device 175 to locate the requested medical study. The server application 165 (using the digital medical image sending routine 170) then automatically sends the client application 115 a digital medical image associated with the requested study (step 220). In one alternative, the server application 165 sends the associated image to the client application 115 upon receiving the request of step 210. In another alternative, upon receiving the request of step 210, the server application 165 sends the client application 115 information about where the associated image is located (e.g., in the storage device 175 of the server device 120 or in another storage location). In contrast to the information that is provided by the user, the location information does not identify a particular medical study; it merely identifies the location of an image associated with the study. The client application 115 then automatically (i.e., without user action) sends another request to the server application 165 to retrieve the image from the location and send it to the client application 115. Once the client application 115 receives the image, the digital medical image display routine 125 automatically presents the image to the user on the display 140 (step 230).

In contrast to the conventional method described in the Background section, the method of this preferred embodiment requires the user to take only one action, namely to provide the client application with information that will identify a particular medical study. This single request triggers the automatic delivery and display of the desired image. Further, the identifying information in the triggering request is not provided by the server application (e.g., from a list generated by the server application), but is provided by the user. Additionally, the request is the only request sent from the client application during the accessing-and-displaying process that identifies the desired medical study. In contrast, the conventional method requires at least two actions from the user. First, the user must provide information that will identify a patient and/or study. Then, after receiving a list of relevant studies, the user must select a study from this list. It is only in response to this second action (the selection step) that the server application provides the image to the client application. Even if the user enters information sufficient to identify one particular study in the first request, he is still required to take the second action of selecting the study from a list (here, the list would comprise only one study).

There are several advantages associated with the method of this preferred embodiment. First, because only one action is required from the user (i.e., providing identification information to the client application), there are fewer steps needed for a user to request and receive the desired image, thereby facilitating the accessing-and-display process. Additionally, because the user is not required to make a second selection from a list of studies, the risk of mistakenly selecting an undesired study is eliminated.

Figure 3:
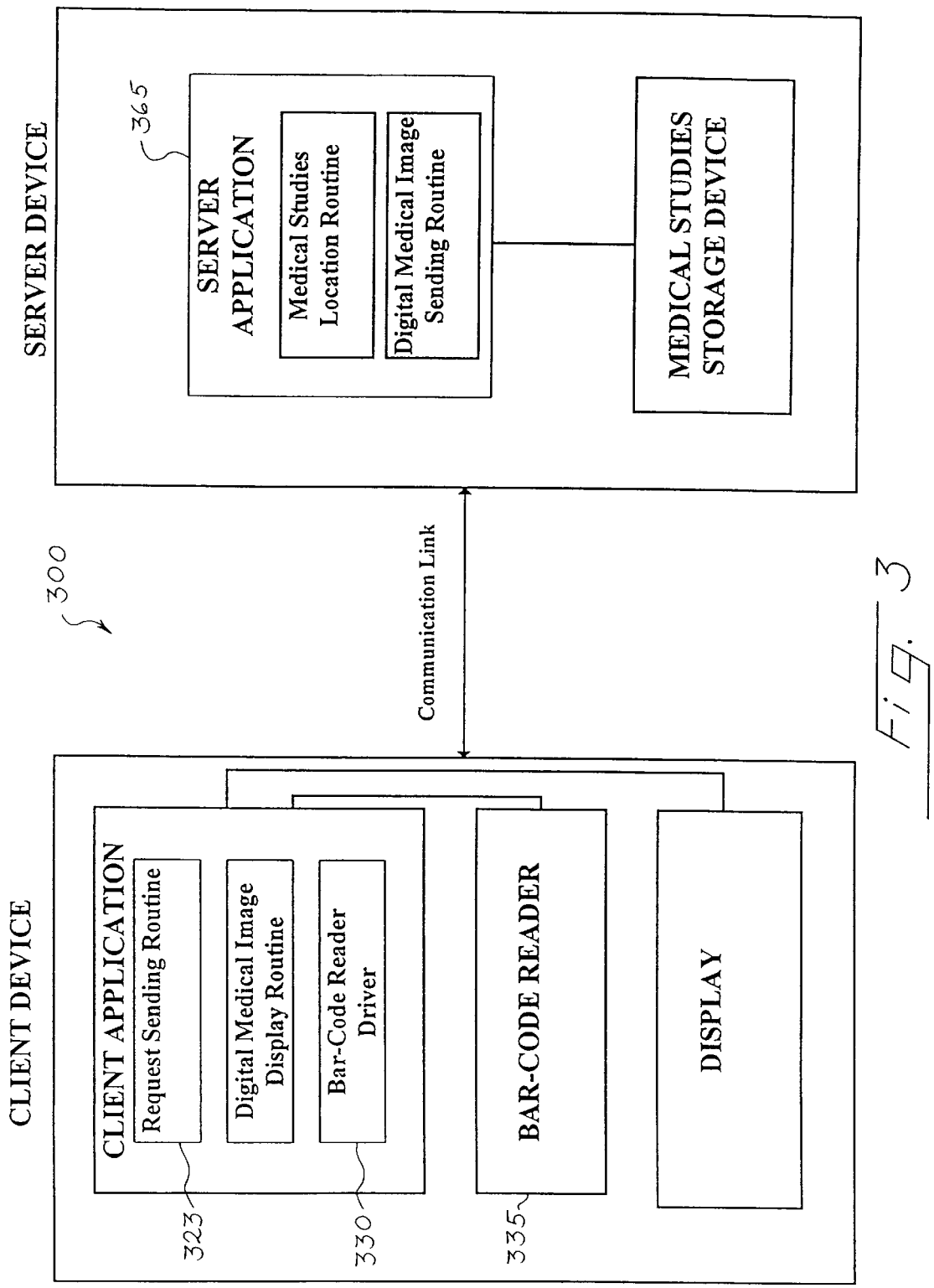
FIG. 3 is a block diagram of a client-server system of a preferred embodiment that uses a bar-code reader as a user interface.

As discussed above, the user interface 135 provides the client application 115 with information that will identify a particular medical study. The user interface 135 can be a keyboard or an automatic information reader. If the user interface 135 is a keyboard, a user must manually enter identification information. To make the process more efficient and to eliminate typographical errors, an automatic information reader can be used as a user interface 135. For example, FIG. 3 shows a client-server system 300 in which a bar-code reader 335 is included in the user interface. With such a system 300, a user uses the bar-code reader (which can be, for example, a free-standing or wand device) to read a bar-code image that contains information needed to identify a particular medical study. In this way, the only action required to request an image is scanning a bar code with the reader 335. The bar-code reader software driver 330 translates the bar-code image into a form (preferably ASCII characters) that the request sending routine 323 can use in its request to the server application 365.

There are several advantages associated with using a bar-code reader as a user interface. Replacing manual data entry eliminates the risk of typographical errors. Also, because a user merely needs to pass a bar code under a reader to request an image, the user does not need system-specific knowledge about the image management system, such as how to manually enter search criteria. In addition to facilitating the access-and-display process, this also reduces the amount of time required to locate and display digital medical images. Further, because a bar-code reader is easy to use, the amount of time needed to train clinical staff is reduced.

Figure 4:
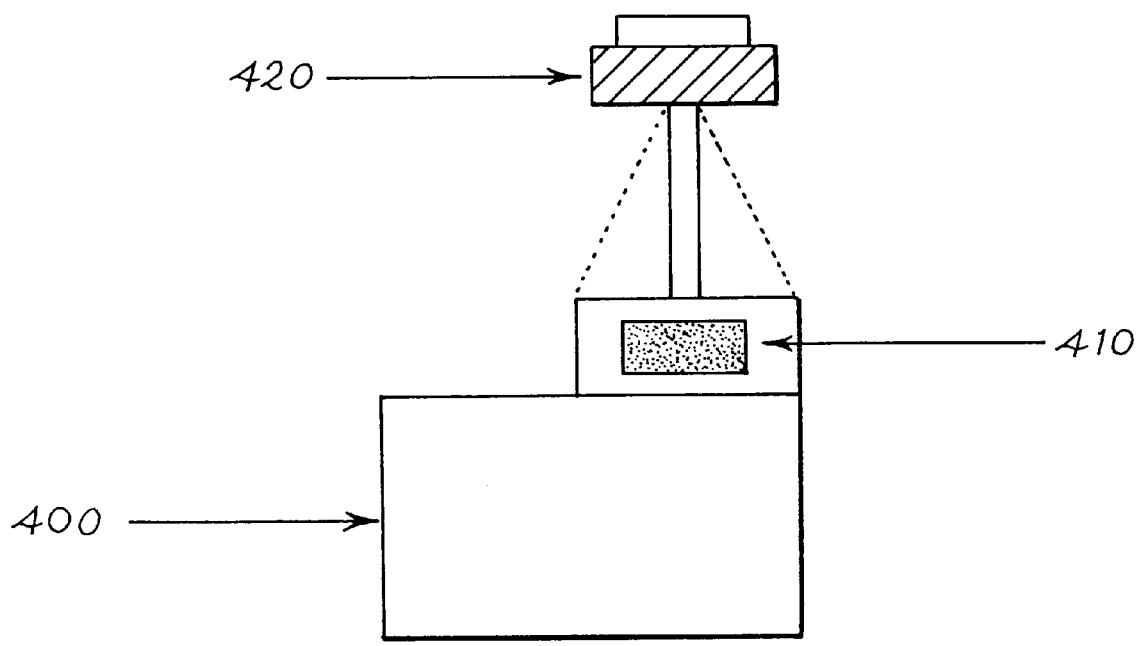
FIG. 4 is an illustration of how a bar-code reader of a preferred embodiment accesses medical study information from a patient file.

Additionally, a client-server system that uses a bar-code reader can be easily installed in a modern medical institution. Many medical institutions use bar-codes on medical patient folders in order to quickly read study information into their information systems. The same bar-code information (such as an accession number) on the medical patient folder can be used to identify a particular medical study. As shown in FIG. 4, a medical patient folder 400 containing a bar code image 410 can easily be placed under a bar-code reader 420 to read the identifying information from the folder 400.

As an alternative to a bar-code reader, other automatic information readers can be used. For example, by using a voice-recognition or sound-communication device, a user can speak the medical study identification information into a microphone. Additionally, a visual-based reading system (such as a digital camera taking a picture of written identification information) can be used. As with a bar-code reader, any of these alternative readers eliminate the risk of typographical errors.

As described above, a digital medical image is a digital image generated by medical imaging equipment. While in one preferred embodiment the digital medical image is an ultrasound image, other digital medical images can be generated by any of the following modalities, computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, radio fluroscopy, or any combination thereof.

It is intended that the foregoing detailed description be understood as an illustration of selected forms that the invention can take and not as a definition of the invention. It is only the following claims, including all equivalents, that are intended to define the scope of this invention.

What is claimed is:

1. A method for accessing and displaying a digital medical image, said method comprising the steps of:
   (a) sending a request comprising information identifying a medical study from a client application to a server application, said information not being provided by the server application; then
   (b) using the server application to automatically send the client application a digital medical image associated with said medical study in response to said request; and then
   (c) using the client application to display said digital medical image.

2. A method for accessing and displaying a digital medical image, said method comprising the steps of:
   (a) sending a user request comprising information identifying a medical study from a client application to a server application, said user request being the only user request sent from the client application during the accessing-and-displaying process to identify said medical study; then
   (b) using the server application to automatically send the client application a digital medical image associated with said medical study in response to said user request; and then
   (c) using the client application to display said digital medical image.

3. The method of claim 1 or 2, further comprising the step of manually providing said information to the client application with a keyboard.

4. The method of claim 1 or 2, further comprising the step of automatically providing said information to the client application with an automatic information reader.

5. The method of claim 1 or 2, further comprising the step of automatically providing said information to the client application with a bar-code reader.

6. The method of claim 1 or 2, further comprising the step of automatically providing said information to the client application with a digital camera.

7. The method of claim 1 or 2, further comprising the step of automatically providing said information to the client application with a voice recognition device.

8. A method for accessing and displaying a digital medical image using a bar-code reader, said method comprising the steps of:
   (a) using a bar-code reader to automatically input information identifying a medical study into a client application; then
   (b) sending a request comprising said information from the client application to a server application; then
   (c) using the server application to automatically send the client application a digital medical image associated with said medical study in response to said request, and then
   (d) using the client application to display said digital medical image.

9. The method of claim 8, wherein said request is the only request sent from the client application during the accessing-and-displaying process to identify said medical study.

10. The method of claim 8, wherein step (a) comprises the step of using said bar-code reader to read a bar-code image on a medical chart.

11. A method for forming a request for a medical study, said method comprising the steps of:
    (a) using a bar-code reader to read a bar-code image comprising information identifying a medical study; and then
    (b) using a client application, coupled with the bar-code reader, to form a request for a medical study using said information.

12. The method of claim 11, wherein said request is the only request formed by the client application during a digital medical image accessing-and-displaying process to identify said medical study.

13. An apparatus for forming a request for a medical study, said apparatus comprising:
    a bar-code reader operative to read a bar-code image comprising information identifying a medical study; and
    a client device, coupled with the bar-code reader, comprising a client application operative to form a request for a medical study using said information.

14. The apparatus of claim 13, wherein said request is the only request formed by the client application during a digital medical image accessing-and-displaying process to identify said medical study.

15. A system for accessing a digital medical image comprising:
    a client device comprising a client application;
    a server device, coupled with the client device, comprising a server application;
    means, included in the client device, for sending a request comprising information identifying a medical study from the client application to the server application, said information not being provided by the server application; and
    means, included in the server application, for automatically sending the client application a digital medical image associated with said medical study in response to said request.

16. A system for accessing a digital medical image comprising:
    a client device comprising a client application;
    a server device, coupled with the client device, comprising a server application;
    means, included in the client device, for sending a user request comprising information identifying a medical study from the client application to the server application, said user request being the only user request formed by the client application during the accessing process to identify said medical study; and
    means, included in the server application, for automatically sending the client application a digital medical image associated with said medical study in response to said user request.

17. The invention of claim 15 or 16, further comprising means, included in the client device, for displaying said digital medical image.

18. The invention of claim 15 or 16, further comprising a bar-code reader, coupled with the client device, operative to input said information into the client application.

19. The invention of claim 15 or 16, further comprising a digital camera, coupled with the client device, operative to input said information into the client application.

20. The invention of claim 15 or 16, further comprising a voice recognition device, coupled with the client device, operative to input said information into the client application.

21. A system for accessing a digital medical image using a bar-code reader comprising:

a client device comprising a client application;

a bar-code reader, coupled with the client application, operative to input information identifying a medical study into the client application;

a server device, coupled with the client device, comprising a server application;

means, included in the client device, for sending a request comprising said information from the client application to the server application; and means, included in the server application, for automatically sending the client application a digital medical image associated with said medical study in response to said request.

22. The invention of claim 21, wherein said request is the only request formed by the client application during the accessing process to identify said medical study.

23. The invention of claim 21 further comprising means, included in the client device, for displaying said digital medical image.

24. The invention of claim 1, 2, 8, 11, 13, 15, 16, or 21, wherein said digital medical image comprises an image created by a modality selected from the group consisting of ultrasound, computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, radio fluroscopy, or any combination thereof.

25. The invention of claim 1, 2, 8, 11, 13, 15, 16, or 21, wherein said information comprises a patient accession number.

* * * * *

UNITED STATES PATENT AND TRADEMARK OFFICE
CERTIFICATE OF CORRECTION

Page 1 of 1

PATENT NO.   : 6,032,120
DATED        : February 29, 2000
INVENTOR(S)  : David A. Rock et al.

It is certified that error appears in the above-identified patent and that said Letters Patent is hereby corrected as shown below:

Specification:
Column 4, line 66, delete "modalities," and substitue --modalities:-- in its place.

Claims:
Claim 8, line 11, delete "request," and substitute --request;-- in its place.
Claim 24, line 3, immediately after "consisting of" insert --:-- (colon).

Signed and Sealed this

Tenth Day of July, 2001

Attest:

NICHOLAS P. GODICI
*Acting Director of the United States Patent and Trademark Office*

*Attesting Officer*